(12) United States Patent
Ninu

(10) Patent No.: US 9,827,116 B2
(45) Date of Patent: Nov. 28, 2017

(54) DEVICE AND METHOD FOR GENERATING A VIBRATION PATTERN

(75) Inventor: Andrei Ninu, Vienna (AT)

(73) Assignee: OTTO BOCK HEALTHCARE PRODUCTS GMBH, Duderstadt (DE)

(*) Notice: Subject to any disclaimer, the term of this patent is extended or adjusted under 35 U.S.C. 154(b) by 450 days.

(21) Appl. No.: 13/386,727

(22) PCT Filed: Jul. 19, 2010

(86) PCT No.: PCT/EP2010/004386
§ 371 (c)(1),
(2), (4) Date: Jan. 24, 2012

(87) PCT Pub. No.: WO2011/009576
PCT Pub. Date: Jan. 27, 2011

(65) Prior Publication Data
US 2012/0119891 A1    May 17, 2012

(30) Foreign Application Priority Data
Jul. 24, 2009   (DE) .................. 10 2009 034 708

(51) Int. Cl.
*A61F 2/50*   (2006.01)
*A61F 2/68*   (2006.01)
(Continued)

(52) U.S. Cl.
CPC ............... *A61F 2/50* (2013.01); *A61B 34/76* (2016.02); *A61F 2/68* (2013.01); *A61F 2002/6827* (2013.01); *A61F 2002/7615* (2013.01)

(58) Field of Classification Search
CPC ...... A61F 2/54; A61F 2/02; A61F 2002/5059; A61F 2002/5061; A61F 2002/5063; A61F 2002/6836; A61F 2002/701; A61F 2002/704; A61F 2002/705; A61F 2002/7635; A61F 2002/764; A61F 2002/7645; A61F 2002/7665;
(Continued)

(56) References Cited

U.S. PATENT DOCUMENTS 5,413,611 A    5/1995   Haslam, II et al.
6,500,210 B1  12/2002   Sabolich et al.
(Continued)

FOREIGN PATENT DOCUMENTS

WO    03091984 A1    11/2003

OTHER PUBLICATIONS

Precision Microdrives™: 10mm Vibration Motor (Flat Type), 1 sheet, Copyright @ 2007, Precision Microdrives Limited.
(Continued)

*Primary Examiner* — Steven Lim
*Assistant Examiner* — Mancil Littlejohn, Jr.
(74) *Attorney, Agent, or Firm* — Holland & Hart

(57) ABSTRACT

The invention relates to a method and a device for generating a vibration pattern in a person, having a drive which sets a mass in rotation, and at least one sensor device which is coupled to a controller which controls the drive as a function of sensor data over the sensor device. The mass (m) is arranged in a homogeneously concentric fashion around its rotational axis (10), and an interface (20) transmits to the person reaction forces from the mass which arise owing to the change in the rotation.

20 Claims, 5 Drawing Sheets

(51) Int. Cl.
*A61B 34/00* (2016.01)
*A61F 2/76* (2006.01)

(58) Field of Classification Search
CPC .............. A61F 2002/6827; H02K 16/04; H02K 7/003; H02K 7/02; H02K 7/04; H02K 7/075
USPC ........ 340/407.1, 407.2, 7.6, 4.1; 601/23, 46, 601/82, 48, 56, 58–60, 66, 67, 71, 72, 78, 601/84, 49; 341/21; 623/24
See application file for complete search history.

(56) References Cited

U.S. PATENT DOCUMENTS

| | | | |
|---|---|---|---|
| 6,504,285 B2* | 1/2003 | Yun | H02K 1/2753 310/193 |
| 8,040,223 B2* | 10/2011 | Mortimer | G06F 3/016 310/71 |
| 8,398,569 B1* | 3/2013 | Mortimer et al. | 601/46 |
| 8,475,172 B2* | 7/2013 | Lieberman et al. | 434/258 |
| 2002/0052663 A1 | 5/2002 | Herr et al. | |
| 2004/0178989 A1 | 9/2004 | Shahoian et al. | |
| 2007/0038311 A1* | 2/2007 | Kuiken | A61F 2/68 623/24 |
| 2008/0200994 A1* | 8/2008 | Colgate | A61F 2/68 623/24 |
| 2008/0288088 A1 | 11/2008 | Langenfeld et al. | |
| 2009/0082705 A1* | 3/2009 | Asfora | 601/46 |

OTHER PUBLICATIONS

PCT International Search Report for International Application No. PCT/EP2010/004386, dated Nov. 9, 2010.

* cited by examiner

DEVICE AND METHOD FOR GENERATING A VIBRATION PATTERN

TECHNICAL FIELD

The invention relates to a device and a method for generating a vibration pattern in a person, having a drive which sets a mass into rotation and at least one sensor apparatus that is coupled to a control which controls the drive dependent on sensor data from the sensor apparatus.

BACKGROUND

U.S. Pat. No. 5,413,611 describes a prosthesis with a feedback apparatus. Feedback relating to the applied force in a driven prosthesis is generated by a vibration generator.

US 2004/0178989 A1 describes a system and a method for providing haptic feedback, in which a motor with an eccentrically arranged mass is put into motion in order to generate a vibration pattern. A similar apparatus is described in WO 03/091984 A1.

SUMMARY

The object of the present invention is to provide a device for generating a vibration pattern and a method, in which complicated feedback patterns can easily be generated. According to the invention, this is achieved by a device with the features of the main claim and by a method with the features of the coordinate claim. Advantageous embodiments and developments of the invention are listed in the dependent claims.

The device according to the invention for generating a vibration pattern in a person, having a drive which sets a mass into rotation and at least one sensor apparatus that is coupled to a control which controls the drive dependent on sensor data from the sensor apparatus, provides for the mass to be arranged in a concentric homogeneous fashion about the rotational axis thereof and for the device to have an interface which transmits the reaction forces to the patient from the mass, which arise as a result of the change in the rotation. The device has a homogeneous concentric mass which is set into rotation by a drive. Here, the generation of the vibration pattern is based on the action/reaction principle. A directed inertia force arises as the result of the acceleration of the rotating mass and initiates a counter movement in a stator about which the concentric mass rotates. The reaction force arising thus generates feedback that can be felt by the user.

The rotating mass is preferably embodied as a rotor which is mounted about a stator of the drive such that the device can be embodied to have a very small design.

The sensor apparatus, which supplies the data on the basis of which the control unit calculates the required magnitude of the swept-through rotor angle, the angular velocity and the acceleration, can be embodied as a pressure sensor, position sensor, torque sensor, movement sensor and/or temperature sensor. As a result, it is possible to record a multiplicity of influences and transmit them to the user of the device by means of a vibration pattern.

By way of example, the sensor apparatus, like the vibration apparatus, can be arranged in or on an exoprosthesis or coupled to an exoprosthesis. Thus, for example, it is possible to process states of the prosthesis elements within the exoprosthesis and, via the device, transmit them to the stump or the attachment point of the prosthesis on the body. Alternative attachment positions of the device are likewise available; in principle, all sufficiently sensitive body points are suitable for this.

An attachment arrangement for attaching the device to the person can be arranged on the device. The attachment arrangement can be embodied as a belt, cuff, or clasp. The vibration pattern may likewise be transmitted to the body by means of a coupling element. The coupling element can concentrate the vibration, for example by coupling the stator to the user of the device by means of an extension or an apparatus with a bearing face that is smaller than the stator. The coupling element, which transmits the reaction forces to the person from the mass, may be arranged in a detachable fashion on the device or be an integral part of the device. To the extent that the coupling element is connected to a stator of the drive via a lever, there can be an adapted vibration transmission. A lever arrangement can likewise make it possible to implement a geared transmission, by means of which the amplitude is increased.

The method according to the invention for generating a feedback signal, in which a sensor signal is provided by at least one sensor apparatus and a mass, arranged concentrically and homogeneously about a rotational axis, is driven depending on the sensor signal, provides for a frequency- and/or amplitude-modulated feedback pattern to be generated. Here, the mass is driven in different rotational directions and with different angular velocities, depending on the sensor signal and, corresponding to this, the feedback pattern to be generated. The mass for generating the feedback pattern is driven with different acceleration patterns depending on the sensor signal, wherein the acceleration patterns can be varied both in terms of a frequency modulation and in terms of an amplitude modulation. The amplitude modulation is regulated by the acceleration of the rotor. The acceleration is regulated on the basis of measured movement variables of the rotor; the greater the rotor acceleration, the higher the amplitude of the stimulation. The frequency is a function of the angular velocity and the swept-through rotor angle. By synchronizing the angular velocity and the swept-through rotor angles, it is possible to modulate the frequency of the stimulation as desired. Here, the frequency may be constant or variable.

It is possible for the signal to be generated in a time-dependent fashion or dependent on a state of the device or the attachment parts thereof. The device can be triggered by specific states of, e.g., the prosthesis. By way of example, an automatic switchover of the prosthesis into another mode can lead to the information in relation to a different prosthesis behavior being transmitted to the wearer of the prosthesis using an appropriate signal. It is likewise possible to indicate specific states, e.g. a charge state of a rechargeable battery, a switched-on prosthesis state or prosthesis components overheating, by a corresponding vibration pattern.

In principle, it is also possible to connect the device to a prosthesis by means of a cable or a radio link. As a result, it is possible to transmit states that are established within a prosthesis to a distant point by means of a vibration pattern. Here, the application of the device is not restricted to transmitting data relating to a prosthesis. It is likewise possible to obtain feedback from exercise equipment or else obtain feedback from myoelectric signals, which were captured by appropriate leads.

In the following text, exemplary embodiments of the invention will be explained in more detail using the attached figures, in which:

DETAILED DESCRIPTION

Figure 1:
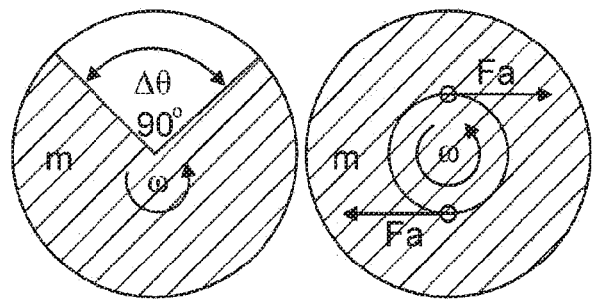
FIG. 1 shows an illustration of the functionality of the device.

FIG. 1 illustrates the basic design of a device for generating a vibration pattern as per the present invention. The device has a homogeneous/concentric mass m which is rotated, by an electric drive (not illustrated) with a swept-through rotor angle $\Delta\theta 9$, the angular velocity $\omega$ and the acceleration $a=d\omega/dt$. The swept-through rotor angle $\Delta\theta$ and the angular velocity $\omega$ are either measured directly by sensors or established indirectly by converting the rotor movement variables. The established rotor position and the current angular velocity are used by a motor control unit 5 (see FIG. 4) for generating predetermined vibration patterns on the basis of sensor data that are provided by a sensor apparatus which does not establish the rotor movements. Thus, this is an apparatus for transmitting feedback by means of vibration patterns, wherein the feedback is generated on the action/reaction principle. A directed inertia force Fa arises according to the formula $Fa=m*a$ as a result of accelerating the rotating mass m. This directed inertia force Fa initiates a counter movement in the stator 15 of the motor. The reaction force arising thereby generates an impulse that can be felt by the user and hence it generates feedback.

Figure 2:
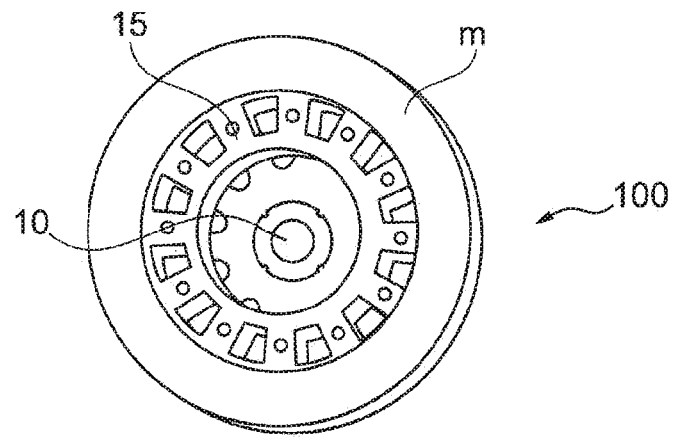
FIG. 2 shows a perspective view or a vibration generator.
Figure 3:
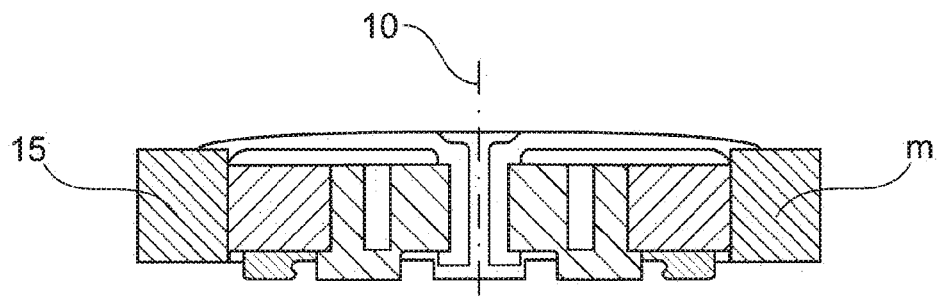
FIG. 3 shows a sectional view.

In a perspective illustration of an embodiment in FIG. 2, the rotating mass m is provided in the form of a ring which is arranged in a concentric and homogenous fashion about the rotational axis 10. The rotational axis 10 is situated in the center of a stator 15, which is embodied as a stator of a motor. Thus, the mass m is part of the drive, namely part of an electric motor. In addition to the illustrated integrated solution, in which the mass m is not mounted separately, there is the option of coupling the drive to the rotatably mounted mass m by means of a gearing mechanism or a transmission. Around the stator 15, the moveable rotor is arranged as a rotating mass m, and so the design here is that of an external-rotor electric motor. In the embodiment as an electronically commutated direct-current motor, the rotating mass m can consist of annularly arranged permanent magnets, or it can have the latter, in order to generate the rotation of the rotating mass m. As a result of an appropriate control of the exciter coils within the stator 15, it is possible to generate a vibration pattern as a feedback pattern in amplitude modulated and/or frequency modulated fashion. Additionally, this affords the possibility of superposing a plurality of modulated feedback patterns and thus of generating a large variety of very complicated feedback patterns, and so a multiplicity of sensor data of very different types can be transmitted to the user of the device 100 in a simple and reliable fashion using feedback patterns of very different types.

The amplitude modulation is regulated by the acceleration of the rotor m. If the rotating mass m is already rotating, the current state is captured by the motor control unit 5 (see FIG. 4). The acceleration is then regulated on the basis of the measured or established movement variables of the rotating mass m such that the directed inertia force Fa is generated as a result of the change in the angular velocity, which inertia force can be transmitted to the user of the device 100 via the stator 15. Within the meaning of both a positive and a negative acceleration, the greater the acceleration of the rotating mass m, the greater the amplitude of the stimulation and the vibration amplitude. If the mass m is initially at rest, the corresponding vibration effect is achieved by acceleration in the one and/or other direction.

The frequency of the generated vibration is a function of the angular velocity $\omega$ and the swept-through rotor angle $\Delta\theta$. By synchronizing the angular velocity $\omega$ and the swept-through rotor angles $\Delta\theta$, it is possible to modulate the frequency of the stimulation as desired. Here, the frequency may either be constant or variable. The frequency of the stimulation emerges from the ratio of the angular velocity $\omega$ to the swept-through rotor angle $\Delta\theta$.

Figure 4:
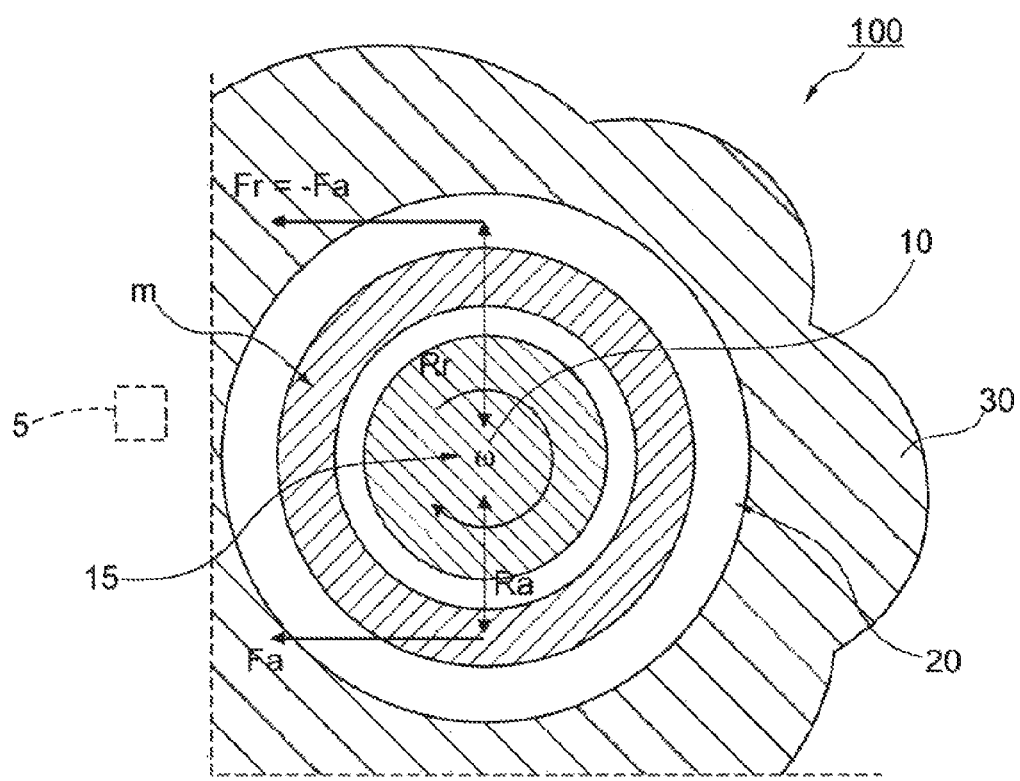
FIG. 4 shows a schematic illustration of a device.

FIG. 4 shows the device 100 in an enlarged and schematic fashion. Here, the device 100 is arranged on the skin surface 30 of a user. The rotating mass m rotates about the rotational axis 10, around which the stator 15 is arranged. In the illustrated exemplary embodiment, the device 100 provides for the mass m to be part of the drive, namely part of the electric motor made of the stator 15 and the rotor that forms the mass m. The stator 15 of the motor generates a rotating magnetic field, as a result of which the rotating mass m is rotated depending on the type of rotating field. Here, the stator 15 is fixed to a housing 20 which forms the interface between the device 100 and the skin surface 30. An appropriate pattern of reaction forces and hence of vibrations is generated depending on rotational direction, frequency and amplitude of the change.

Figure 5:
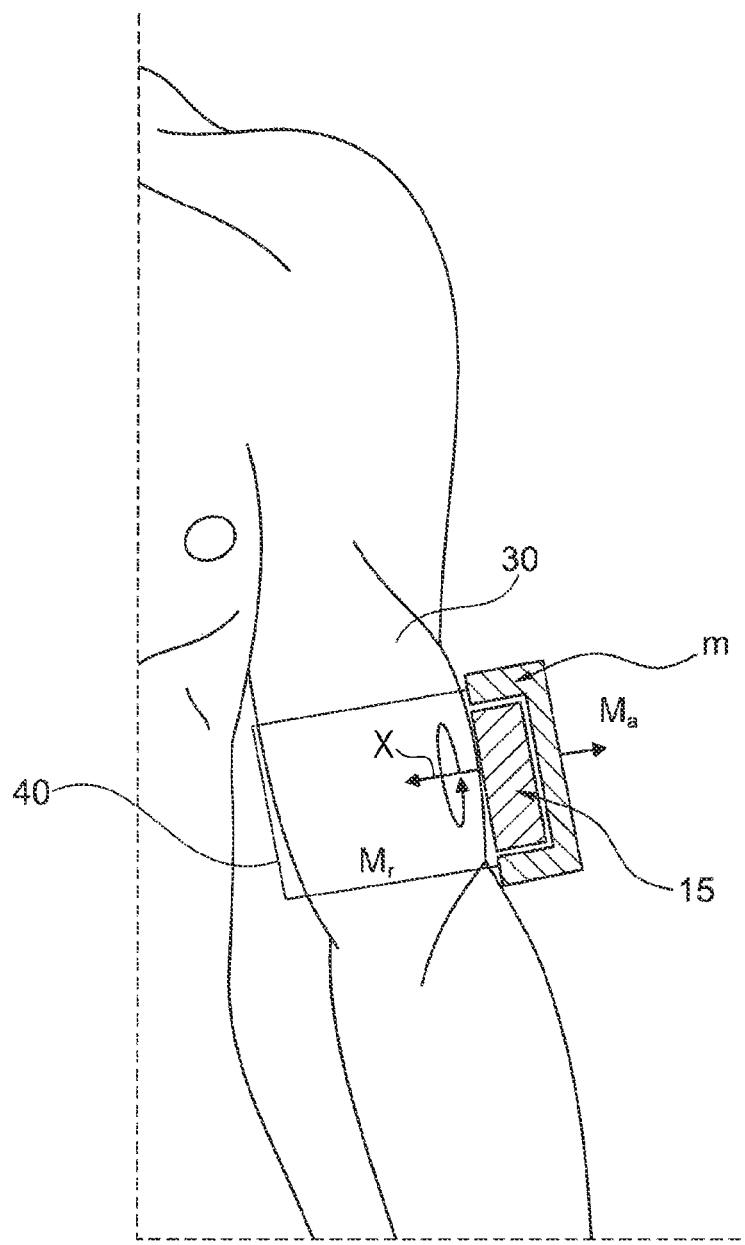
FIG. 5 shows an illustration of an applied device.

Here, FIG. 5 shows the device 100 in the applied state. In FIG. 5, the device 100 has been applied to an upper part of the arm by means of an attachment arrangement 40 in the form of a cuff. FIG. 5 also shows the acting torques about a rotation axis X of the mass m. The rotation axis X is shown in FIG. 5 arranged substantially perpendicular to the attachment arrangement 40 and to a skin surface 30 of the body part (i.e., upper arm) to which the device 100 is mounted. The reaction torque Mr is exerted on the interface, i.e. the housing 20, by the rotating mass m. The magnitude of the torque Mr is defined by the moment of inertia of the rotating, homogeneous concentric mass m and the force or acceleration acting thereon.

Figure 6:
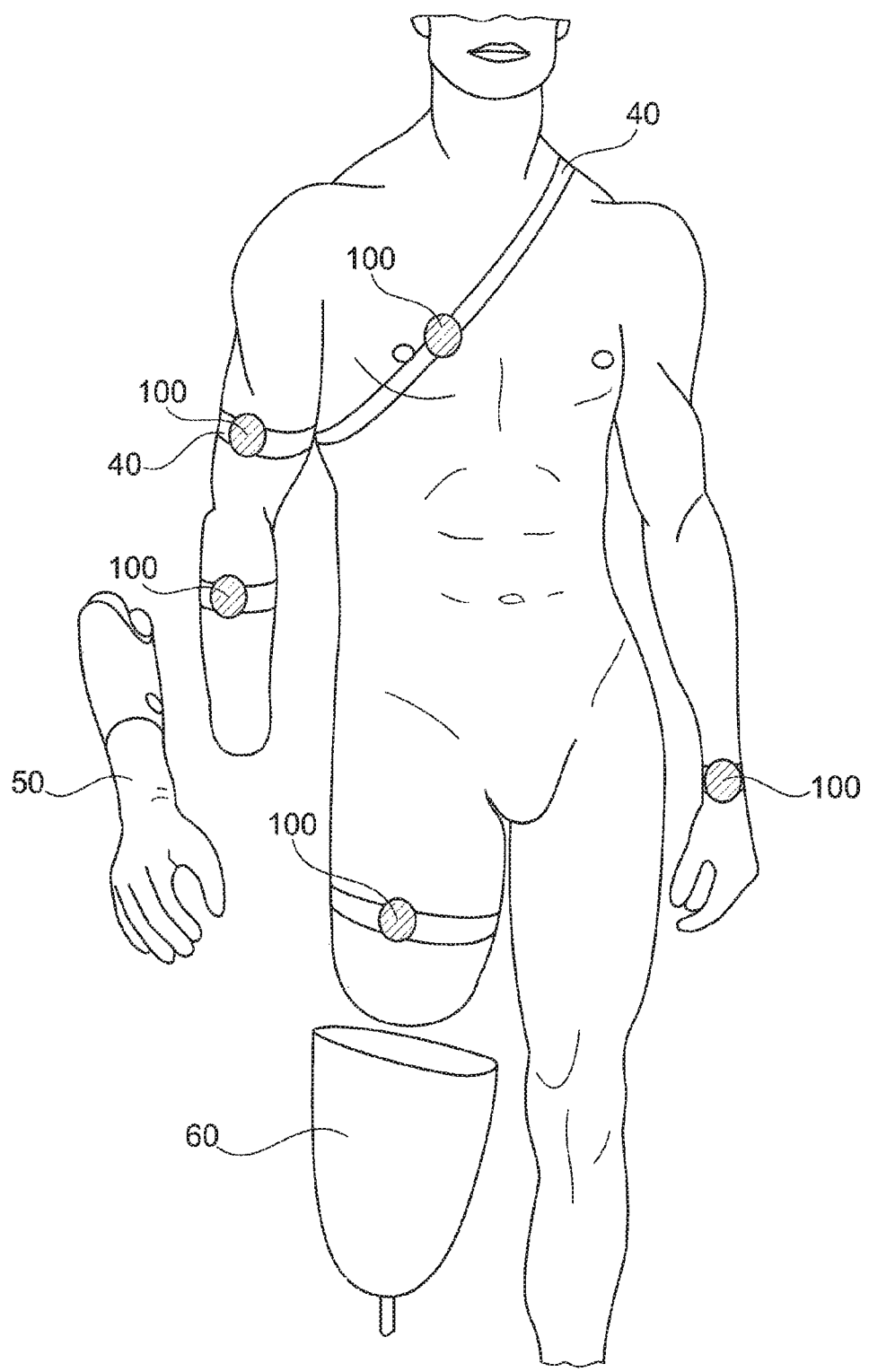
FIG. 6 shows different arrangements on a person.

FIG. 6 shows different attachment points of the device 100, for example on the wrist, on the chest, on the upper part of the arm, on the forearm or on the thigh. It is likewise possible to arrange the device directly in a prosthesis apparatus 50, 60, for example in a forearm prosthesis 50 or in a thigh shaft 60 of a leg prosthesis.

Figure 7:
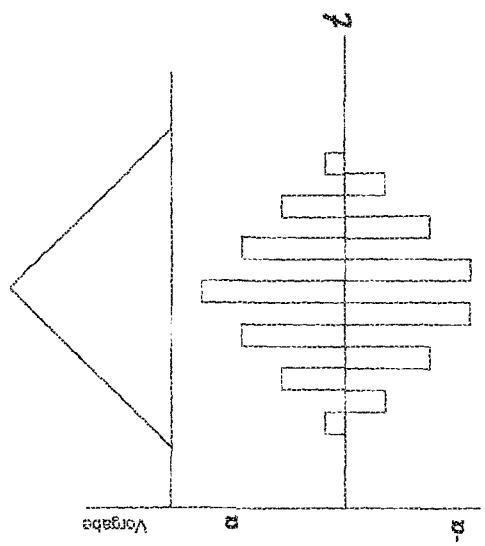
FIG. 7 shows illustrations of frequency modulations and amplitude modulations.
Figure 7:
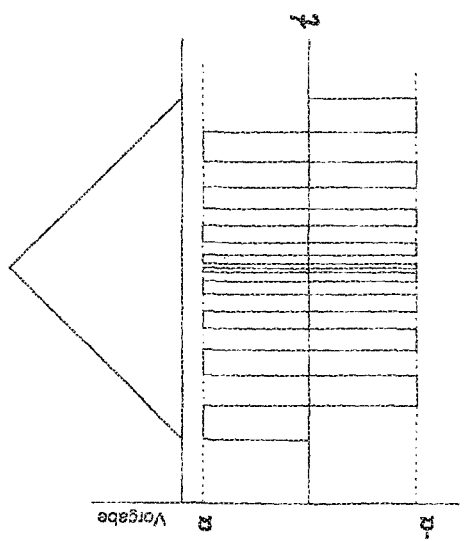

FIG. 7 illustrates a frequency modulation and an amplitude modulation. In the case of a stepwise acceleration a with an unchanging magnitude there is no change in the strength of the vibration impulse; since, over time, the acceleration or deceleration or movement reversal occurs at ever shorter time intervals, the vibration frequency increases such that the user of the device obtains feedback which is generated depending on the measured sensor signals. The positive and negative acceleration a either means that the rotational direction is reversed or that the mass is accelerated and decelerated about a basic velocity.

By contrast, the right-hand illustration of FIG. 7 shows an amplitude modulation in which the measure of the acceleration a is varied without changing the frequency. In the illustrated exemplary embodiment, this initially leads to a weak vibration being transmitted to the user, which vibration increases over time until it decreases again after reaching the maximum. By superposing the frequency modulation and the amplitude modulation, it is possible to generate multifaceted signal patterns and transmit these to the user of the device.

In addition to data, e.g. in respect of the state of a prosthesis apparatus 50, 60, for example the current grip force, it is possible to transmit other data to the user via the device 100, for example state data relating to temperature, switch-on states, operating modes, battery states or the like. It is likewise possible to process myoelectric data, recorded by leads, and transmit these on to the user as vibration signals, for example to be able to carry out optimized training.

The invention claimed is:

1. A device for generating a vibration pattern in a person, the device comprising:
 a concentric homogeneous mass;
 a drive which sets the mass into rotation about a rotational axis of the mass, wherein the rotational axis is configured to be arranged substantially perpendicular to a body part of the person to which the device is mounted;
 at least one sensor apparatus;
 a control configured to control the drive dependent on sensor data received from the sensor apparatus;
 an interface configured to transmit reaction forces to the person from the mass, which arise as a result of a change in rotation of the mass, the reaction forces creating the vibration pattern in the person;
 wherein the drive is interposed between the mass and the interface, and the reaction forces are transmitted through the drive to the interface.

2. The device as claimed in claim 1, wherein the drive is an electric motor.

3. The device as claimed in claim 1, wherein the rotating mass is embodied as a rotor which is mounted about a stator of the drive.

4. The device as claimed in claim 1, wherein the sensor apparatus is embodied as at least one of a pressure sensor, position sensor, torque sensor, movement sensor and temperature sensor.

5. The device as claimed in claim 1, wherein the sensor apparatus is arranged in an exoprosthesis.

6. The device as claimed in claim 1, wherein the device is arranged in or on an exoprosthesis or coupled to the exoprosthesis.

7. The device as claimed in claim 1, further comprising an attachment arrangement for attaching the device to the person.

8. The device as claimed in claim 1, further comprising at least one coupling element which transmits the reaction forces to the person from the mass.

9. The device as claimed in claim 8, wherein the at least one coupling element is connected to a stator of the drive via a lever.

10. A method for generating a feedback signal, comprising:
 providing a device having at least one sensor apparatus, a drive, an interface and a concentric homogeneous mass, the mass being arranged concentrically and homogeneously about a rotational axis of the mass, the rotational axis being configured to be arranged substantially perpendicular to a body part of a person to which the device is mounted, the drive being interposed between the mass and the interface;
 generating a sensor signal with the at least one sensor apparatus;
 driving the mass with the drive in response to the sensor signal in order to generate at least one of a frequency-modulated feedback pattern and an amplitude-modulated feedback pattern which are transmitted through the drive to the interface.

11. The method as claimed in claim 10, wherein the mass is driven in different rotational directions.

12. The method as claimed in claim 10, wherein the mass is driven with different acceleration patterns depending on the sensor signal.

13. The method as claimed in claim 10, wherein a plurality of feedback patterns are superposed on one another.

14. The method as claimed in claim 10, wherein the sensor signal is generated in a time-dependent fashion or dependent on a state of the device or attachment parts of the device.

15. A device for generating a vibration pattern in a person, the device comprising:
 a concentric homogeneous mass operable to generate reaction forces resulting from a change in rotation of the mass;
 a drive operable to set the mass into rotation about a rotational axis of the mass, the rotational axis being configured to be arranged substantially perpendicular to a body part of the person to which the device is mounted;
 at least one sensor apparatus configured to generate sensor data corresponding to at least one property of the device;
 a control configured to control the drive based on the sensor data;
 an interface configured to transmit reaction forces to the person from the mass, the reaction forces creating the vibration pattern in the person;
 wherein the drive is interposed between the mass and the interface, and the reaction forces are transmitted through the drive to the interface.

16. The device as claimed in claim 15, wherein the drive is an electric motor.

17. The device as claimed in claim 15, wherein the mass is embodied as a rotor which is mounted about a stator of the drive.

18. The device as claimed in claim 15, wherein the sensor apparatus is embodied as at least one of a pressure sensor, position sensor, torque sensor, movement sensor and temperature sensor.

19. The device as claimed in claim 15, wherein the sensor apparatus is arranged in an exoprosthesis.

20. The device as claimed in claim 15, wherein the device is arranged in or on an exoprosthesis or coupled to the exoprosthesis.

* * * * *